United States Patent
Prien et al.

(10) Patent No.: US 11,169,064 B2
(45) Date of Patent: Nov. 9, 2021

(54) SYSTEM AND METHOD FOR ASSESSING EMBRYO VIABILITY

(71) Applicant: TEXAS TECH UNIVERSITY SYSTEM, Lubbock, TX (US)

(72) Inventors: Samuel D. Prien, Shallowater, TX (US); Lindsay L. Penrose, Lubbock, TX (US)

(73) Assignee: Texas Tech University System, Lubbock, TX (US)

( * ) Notice: Subject to any disclaimer, the term of this patent is extended or adjusted under 35 U.S.C. 154(b) by 0 days.

(21) Appl. No.: 15/323,017

(22) PCT Filed: Jun. 30, 2015

(86) PCT No.: PCT/US2015/038665
§ 371 (c)(1),
(2) Date: Dec. 29, 2016

(87) PCT Pub. No.: WO2016/004107
PCT Pub. Date: Jan. 7, 2016

(65) Prior Publication Data
US 2018/0172572 A1    Jun. 21, 2018

Related U.S. Application Data

(60) Provisional application No. 62/019,034, filed on Jun. 30, 2014.

(51) Int. Cl.
*G01N 9/36* (2006.01)
*C12N 5/073* (2010.01)
*G01N 33/483* (2006.01)

(52) U.S. Cl.
CPC .............. *G01N 9/36* (2013.01); *C12N 5/0604* (2013.01); *G01N 33/483* (2013.01); *G01N 33/4833* (2013.01); *C12N 2525/00* (2013.01)

(58) Field of Classification Search
CPC ...... C12N 5/00; C12N 5/0603; C12N 5/0604; G01N 33/483; G01N 33/4833; G01N 9/36
See application file for complete search history.

(56) References Cited

FOREIGN PATENT DOCUMENTS

GB         2 070 437 A   *  9/1981

OTHER PUBLICATIONS

Weathers, "Early indication of Breed Differences for Cryopreservation of Embryos in Cattle", Thesis, Texas Tech University, Aug. 2008. (Year: 2008).*
American Association of Bioanalysts—Embryo Grading Proficiency Testing. http://www.aab-pts.org/pdf/stats/EmbAnds12013/AEF%20Embryo%20Grading%20Qualitative%201Q2013.pdf.
Abe H., Yamashita S., Satoh T., Hoshi H. Accumulation of cytoplasmic lipid droplets in bovine embryos and cryotolerance of embryos developed in different culture systems using serum-free or serum-containing media. Mol. Reprod. Dev. 2002; 61: 57-66.
Al Inany H, Aboulghar M, Mansour R, Serour G. Meta-analysis of recombinant versus urinary-derived FSH: an update. Hum Reprod. 2003;18:305-313. doi: 10.1093/humrep/deg088.
Alfarawati S, Fragouli E, Colls P, Wells D. First births after preimplantation genetic diagnosis of structural chromosome abnormalities using comparative genomic hybridization and microarray analysis. Hum Reprod. 2011;26:1560-74. doi: 10.1093/humrep/der068.
Alfarawati S, Fragouli E, Colls P, Stevens J, Gutierrez-Mateo C, Schoolcraft WB, Katz-Jaffe MG, Wells D. The relationship between blastocyst morphology, chromosomal abnormality, and embryo gender. Fertil Steril. 2011;95:520-4.
Baltz JM. Connections between preimplantation embryo physiology and culture. J Assist Reprod Genet. Aug. 2013;30(8):1001-7.
Barcelo-Fimbres M., Seidel G. E. Jr. Effects of either glucose or fructose and metabolic regulators on bovine embryo development and lipid accumulation in vitro. Mol. Reprod. Dev. 2007; 74: 1406-1418.
Brezina PR. Preimplantation Genetic Testing in the 21st Century: Uncharted Territory. Clin Med Insights Reprod Health. 2013;7:17-21.
Brison DR, Houghton FD, Falconer D, Roberts SA, Hawkhead J, Humpherson PG, Lieberman BA, Leese HJ. Identification of viable embryos in IVF by non-invasive measurement of amino acid turnover. Hum Reprod 2004; 19:2319-2324.
Bühler KF, Fischer R. Recombinant human LH supplementation versus supplementation with urinary hCG-based LH activity during controlled ovarian stimulation in the long GnRH-agonist protocol: a matched case-control study. Gynecol Endocrinol. May 2012;28(5):345-50. doi: 10.3109/09513590.2011.633128.
Centers for Disease Control—Assisted Reproductive Technologies (ART). 2013. http://www.cdc.gov/art/.
Chandra A, Martinez GM, Mosher WD, Abma JC, Jones J. Fertility, family planning, and reproductive health of U.S. women: Data from the 2002 National Survey of Family Growth. National Center for Health Statistics. Vital Health Stat 23(25). 2005.
Chavez SL, Loewke KE, Han J, Moussavi F, Colls P, Munne S, Behr B, Reijo Pera RA. Dynamic blastomere behaviour reflects human embryo ploidy by the four-cell stage. Nat Commun. 2012;3:1251 doi: 10.1038/ncomms2249.
Conaghan J, Chen AA, Willman SP, Ivani K, Chenette PE, Boostanfar R, VL, Adamson GD, Abusief ME, Gvakharia M, Loewke KE, Shen S. Improving embryo selection using a computer-automated time-lapse image analysis test plus day 3 morphology: results from a prospective multicenter trial. Fertil Steril. 2013;100:412-9.e5. doi:10.1016/j.fertnstert.2013.04.021.

(Continued)

*Primary Examiner* — Ruth A Davis
(74) *Attorney, Agent, or Firm* — Dickinson Wright PLLC; Kristopher Lance Anderson

(57) ABSTRACT

Disclosed is a system for determining fecundity of an embryo utilizing a non¬ invasive grading of early stage embryos (pre-hatching) based upon specific gravity, density and/or estimated weight. The system allows 100% recovery of embryos and can detect differences in growth potential at the earliest stages of development. The system may further enhance the development of embryos by utilization of microfluidic effects during use. The disclosed system supports a wide variety of scenarios for human and animal reproductive technologies and related products and services.

8 Claims, 5 Drawing Sheets

(56) References Cited

OTHER PUBLICATIONS

Das M, Holzer HE. Recurrent implantation failure: gamete and embryo factors. Fertil Steril. May 2012;97 (5):1021-7. doi: 10.1016/j.fertnstert.2012.02.029.

Deonandan R, Campbell MK, Østbye T, Tummon I. Toward a more meaningful in vitro fertilization success rate. J Assist Reprod Genet. Oct. 2000;17(9):498-503.

Ercan CM, Kerimoglu OS, Sakinci M, Korkmaz C, Duru NK, Ergun A. Pregnancy outcomes in a university hospital after legal requirement for single-embryo transfer. Eur J Obstet Gynecol Reprod Biol. 2014; pii: S0301-2115 (14)00031-1. doi: 10.1016/j.ejogrb.2014.01.008.

Filicori M, Cognigni G.E., Pocognoli P, Tabarelli C, Ferlini F, Perri T, Parmegiani L. Comparison of controlled ovarian stimulation with human menopausal gonadotropin or recombinant follicle-stimulating hormone. Fertil Steril. 2003;80:390-397. doi: 10.1016/S0015-0282(03)00594-6.

Gardner DK, Leese HJ. Assessment of embryo viability prior to transfer by the noninvasive measurement of glucose uptake. J Exp Zool 1987; 242:103-105.

Gardner DK, Wale PL. Analysis of metabolism to select viable human embryos for transfer. Fertil Steril. Mar. 15, 2013;99(4):1062-72. doi: 10.1016/j.fertnstert.2012.12.004.

Geber S, Bossi R, Guimaraes F, Valle M, Sampaio M. Effects of transfer of embryos independently cultured in essential and sequential culture media on pregnancy rates in assisted reproduction cycles. J Assist Reprod.

Genet. Oct. 2012;29(10):1097-101. doi: 10.1007/s10815-012-9835-6.Gerris J, De Neubourg D, Mangelschots K, et al. Prevention of twin pregnancy after in-vitro fertilization or intracytoplasmic sperm injection based on strict embryo criteria: a prospective randomized clinical trial. Hum Reprod 1999; 14:2581-2587.

Grace J, El-Toukhy T, Scriven P, Ogilvie C, Pickering S, Lashwood A, Flinter F, Khalaf Y, Braude P.Three hundred and thirty cycles of preimplantation genetic diagnosis for serious genetic disease: clinical considerations affecting outcome. BJOG. 2006;113:1393-401.

Houghton FD, Hawkhead JA, Humpherson PG, Hogg JE, Balen AH, Rutherford AJ, Leese HJ. Non-invasive amino acid turnover predicts human embryo developmental capacity. Hum Reprod 2002; 17:999-1005.

Hur YS, Park JH, Ryu EK, Park SJ, Lee JH, Lee SH, Yoon J, Yoon SH, Hur CY, Lee WD, Lim JH. Effect of micro-vibration culture system on embryo development. J Assist Reprod Genet. 2013;30:835-41. doi: 10.1007/s10815-013-0007-0.

Kresowik JD, Sparks AE, Van Voorhis BJ. Clinical factors associated with live birth after single embryo transfer. Fertil Steril. 2012;98:1152-6 doi: 10.1016/j.fertnstert.2012.07.1141.

Janvier A, Spelke B, and Barrington K. The Epidemic of Multiple Gestations and Neonatal Intensive Care Unit Use: The Cost of Irresponsibility. J Pediatr2011; 159:409-13.

Jones GM, Trounson A, Vella PJ, Thouas GA, Lolatgis N, Wood C. Glucose metabolism of human morula and blastocyst-stage embryos and its relationship to viability after transfer. RBM Online 2001; 3:124-132.

Lane M, Gardner DK. Selection of viable mouse blastocysts prior to transfer using a metabolic criterion. Hum Reprod 1996; 11:1975-1978.

Luke B, Brown MB, Wantman E, Lederman A, Gibbons W, Schattman GL, Lobo RA, Leach RE, Stern JE. Cumulative birth rates with linked assisted reproductive technology cycles. N Engl J Med. 2012;366:2483-91. doi: 10.1056/NEJMoa1110238.

Machtinger R, Racowsky C. Morphological systems of human embryo assessment and clinical evidence. Reprod Biomed Online. 2013;3:210-21. doi: 10.1016/j.rbmo.2012.10.021.

McArthur SJ, Leigh D, Marshall JT, de Boer KA, Jansen RP. Pregnancies and live births after trophectoderm biopsy and preimplantation genetic testing of human blastocysts Fertil Steril 2005;84:1628-36.

Muñoz G, Bongiorni-Malavé I.Influence of dietary protein restriction on ovulation, fertilization rates and pre-implantation embryonic development in mice. J Exp Zool. 1979 ;210:253-257.

Racowsky C, Vernon M, Mayer J, Ball GD, Behr B, Pomeroy KO, Ball GD, Behr B, Pomeroy KO, Wininger D, Gibbons W, Conaghan J, Stem JE. Standardization of grading embryo morphology. J Assist Reprod Genet. 2010 ;27:437-9. doi: 10.1007/s10815-010-9443-2.

Reynolds KA, Omurtag KR, Jimenez PT, Rhee JS, Tuuli MG, Jungheim ES. Cycle cancellation and pregnancy after luteal estradiol priming in women defined as poor responders: a systematic review and meta-analysis. Hum Reprod. 2013;28:2981-9. doi: 10.1093/humrep/det306.

Sakkas, D. and Gardner, D.K. Noninvasive methods to assess embryo quality. CurrOpin Obstet Gynecol 2005;17:283-288.

Scott RT Jr, Upham KM, Forman EJ, Hong KH, Scott KL, Taylor D, Tao X, Treff NR. Blastocyst biopsy with comprehensive chromosome screening and fresh embryo transfer significantly increases in vitro fertilization implantation and delivery rates: a randomized controlled trial. Fertil Steril. 2013;100:697-703. doi: 10.1016/j.fertnstert.2013.04.035.

Staessen C, Platteau P, Van Assche E, Miciels A, Tournaye H, Camus M, Devroey P, Liebaers I, van Steirteghem A: Comparison of blastocyst transfer with and without preimplantation genetic diagnosis for aneuploidy screening in couples with advanced maternal age: a prospective randomized controlled trial Hum Reprod 2004, 19:2849-2858.

Steptoe PC, Edwards RG, Purdy JM. Clinical aspects of pregnancies established with cleaving embryos grown in vitro. Br J Obstet Gynaecol. 1980;87:757-68.

Smith AL. Blastocyst culture in human IVF: the final destination or a stop along the way? Theriogenology. 2002;57:97-107.

Smith GD, Monteiro da Rocha A. Advances in embryo culture systems. Semin Reprod Med. 2012;30:214-21. doi: 10.1055/S-0032-1311523.

Thompson SM, Onwubalili N, Brown K, Jindal SK, McGovern PG. Blastocyst expansion score and trophectoderm morphology strongly predict successful clinical pregnancy and live birth following elective single embryo blastocyst transfer (eSET): a national study. J Assist Reprod Genet. 2013;12:1577-81. doi: 10.1007/s10815-013-0100-4.

Van den Abbeel E, Balaban B, Ziebe S, Lundin K, Cuesta MJ, Klein BM, Helmgaard L, Arce JC. Association between blastocyst morphology and outcome of single-blastocyst transfer. Reprod Biomed Online. 2013; 4:353-61. doi: 10.1016/j.rbmo.2013.07.006.

Weathers, J. (2008) Early Indications of Breed Differences for Cryopreservation of Embryos in Cattle. Master's Thesis. repositories.tdl.org/ttu-ir/bitstream/handle/2346/18883/Weathers_Julie_Thesis.pdf?sequence=1.

Weathers, N. Zimmerer N., Penrose L., Graves-Evenson K., Prien, S.. The relationship between maternal body fat and pre-implantation embryonic weight: Implications for survival and long-term development in an assisted reproductive environment. Open J Ob Gyn, 2013, 3; 1-5. doi:10.4236/ojog.2013.35A2001.

\* cited by examiner

SYSTEM AND METHOD FOR ASSESSING EMBRYO VIABILITY

CROSS-REFERENCE TO RELATED APPLICATIONS

This application claims priority to: provisional U.S. Patent Application Ser. No. 62/019,034, filed on Jun. 30, 2014, entitled "System for Determining Embryo Viability" which provisional patent application is commonly assigned to the Assignee of the present invention and is hereby incorporated herein by reference in its entirety for all purposes.

This application includes material that is subject to copyright protection. The copyright owner has no objection to the facsimile reproduction by anyone of the patent disclosure, as it appears in the Patent and Trademark Office files or records, but otherwise reserves all copyright rights whatsoever.

TECHNICAL FIELD

The present invention relates in general to the field of assisted reproductive technologies. In particular, the system provides for viability testing of embryos. The disclosed systems and methods support a wide variety of scenarios for human reproductive medicine and animal husbandry related products and services.

STATEMENT OF FEDERALLY FUNDED RESEARCH

None.

BACKGROUND OF THE DISCLOSURE

Assisted reproductive technologies (ARTs) were developed originally to treat individuals with obstructed tubes, but have matured to procedures which, according to the U.S. Center for Disease Control (2013), now accounts for up to 2% of the annual U.S. birth rate. Since the first human birth from in vitro fertilization (IVF) in 1978, there have been significant improvements in stimulation protocols, fertilization and culture techniques, use of donor gametes and embryos, and patient selection. Further, the use of pre-implantation genetic diagnosis/pre-implantation genetic screening (PGD/PGS), an invasive harvesting of cells for genetic screening, has allowed improved selection of embryos to avoid aneuploidy and other genetic defects. These improvements resulted in constantly increasing pregnancy rates while allowing a steady decrease in the number of embryos transferred (Center for Disease Control, 2013).

However, even with the dramatic improvement in pregnancy rates from ART over the last 35 years, two issues remain problematic for patients and healthcare professionals using ART: 1) multiple gestations and 2) the fecundity of individual embryos. To solve the first of these issues, ART now appears poised for a paradigm shift, the routine use of single embryo transfer (SET). In order to become the standard of care, a solution must be found to the second issue, individual embryo fecundity. Traditionally, embryo quality has been based solely on embryo morphology or embryo morphology coupled with expected growth rates. However, there remains significant disagreement as to what constitutes a "normal embryo". Further, while the addition of pre-implantation genetic diagnosis (PGD) has improved the selection process, it is an invasive technique which requires significant equipment and expertise, has an identified risk for embryo damage, and while it can diagnose genetic defect, it does not ensure fecundity. Given the cost of the procedures, risks associated with medications and surgical procedures, and the emotional toll negative pregnancy results have on couples, any improvement in embryo selection which is non-invasive, less subjective and leads to higher pregnancy rates, while limiting the risk of multiple gestations, would represent a significant improvement in women's reproductive health.

Despite advances in the art, there remains a need to improve embryo selection by establishing the viability and fecundity of individual embryos.

SUMMARY OF THE DISCLOSURE

Recent techniques have been developed which can estimate the weight of an embryo based on specific gravity. Preliminary data using the specific gravity system (the device of the present invention) suggested that cryopreserved cattle blastocysts from animals with known differences in body composition have significantly different estimated weights. These differences appeared to be due to lipid content within the embryos. Further testing with fresh mouse embryos at various stages of pre-implantation development (zygote to blastocyst), appeared to confirm this observation, both using a series of mouse strains with genetically different weights and a single strain with animals of different weights. However, in both of these studies there were embryos with estimated weights significantly higher or lower than those of the established population mean (i.e., >2 SDs from the mean).

It is therefore an object of the present invention to determine if observed differences in estimated weight within a cohort of embryos could be used to select high quality embryos for ART procedures. The present invention determines differences seen in estimated zygote weights to 1) distinguish viable from non-viable embryos, 2) predict future development, and 3) demonstrate that the technique did not negatively impact growth rates compared to a control population.

The present invention addresses the limitations of the art by providing a system for the non-invasive grading of early stage embryos (pre-hatching) based upon specific gravity, density and/or estimated weight. The system allows 100% recovery of embryos and can detect differences in growth potential at the earliest stages of development. The system may include drop chamber extending into to a collection pool to allow for recovery of embryos. Further, the system can be filled with an embryo culture media of users choosing and compatible with embryo survival outside of controlled culture conditions.

It is therefore an object of the present invention to provide a device for assessment of mammalian embryos, comprising: a base having an internal collection pool; a tube extending vertically from the base; and a biocompatible media composition; wherein the tube comprises a lumen for passing embryos for purposes of said assessment.

It is another object of the present invention to provide a method of assessing of mammalian embryos, comprising: passing one or more embryos through a tube comprising a lumen extending vertically from a media collection pool; and assessing the embryos by observing said descent through said tube.

It is another object of the present invention to provide a system for enhancing mammalian embryo development comprising: inserting one or more embryos into a tube comprising a lumen extending vertically from a media collection pool, wherein the tube comprises a biocompatible media composition; and allowing said one or more embryos to descend through said tube; wherein the descent creates a microfluidic effect which enhances embryo development.

The system of the present invention may further include a pressure seal to allow the media to be continuous from the top of the drop chamber to collection pool. The system has a "timing zone" to determine the descent time of the embryo over a known distance.

Additionally, the system drains media from the drop chamber into the recovery pool, which may be referred to as a collection pool, upon breaking of the pressure seal to ensure flushing of the embryo into the recovery pool. It is a preferred embodiment of the present invention that said system potentially increases the embryo growth rate over static culture. The system may further comprise rotating, revolving, carousel, or otherwise multiple-welled or multiple-strawed configurations, allowing for the ability of the drop chamber (the tube) to have multiple chambers, each having its own collection pool, or collection pool to allow collection of information about individual embryos. In another aspect, the system provides the ability to have a single drop chamber (the tube) positioned at various times over multiple collection pools to allow collection of information about individual embryos while allowing a single chamber's use.

BRIEF DESCRIPTION OF THE DRAWINGS

The foregoing and other objects, features, and advantages of the disclosure will be apparent from the following description of embodiments as illustrated in the accompanying drawings, in which reference characters refer to the same parts throughout the various views. The drawings are not necessarily to scale, emphasis instead being placed upon illustrating principles of the disclosure.

DETAILED DESCRIPTION OF THE DISCLOSURE

Figures 1A, 1B:
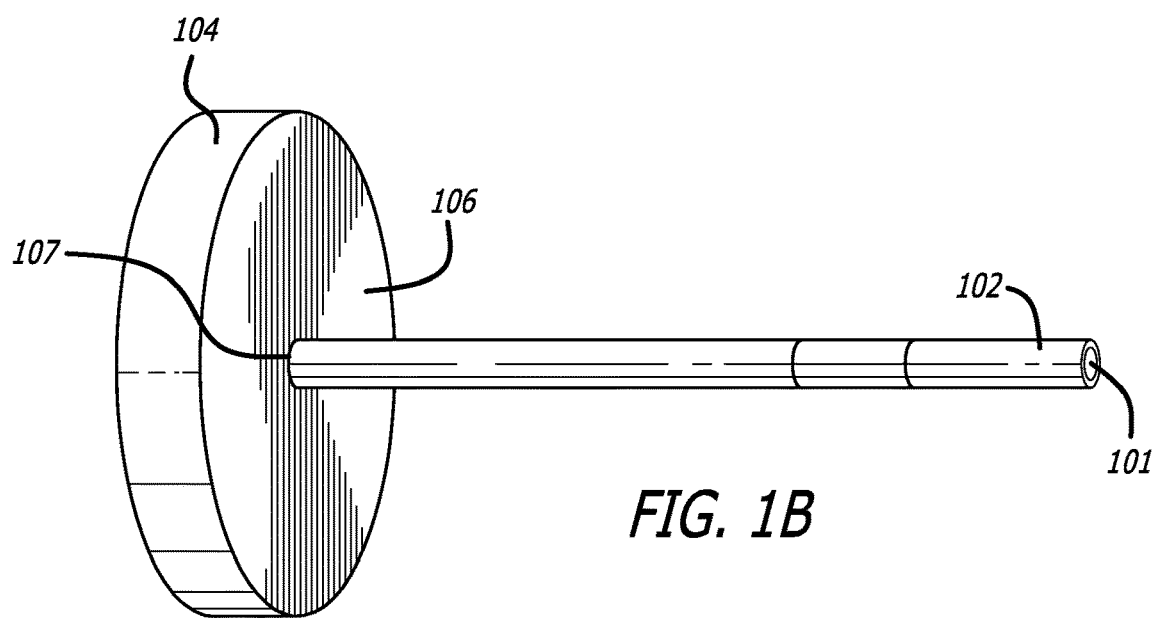
FIG. 1A depicts the device of the present invention as designed for use (note lid has been removed from diagram for ease of visualization).
FIG. 1B depicts the device of the present invention in a form factor having a removable lid configuration and positioned horizontally.

While the making and using of various embodiments of the present invention are discussed in detail below, it should be appreciated that the present invention provides many applicable inventive concepts that can be embodied in a wide variety of specific contexts, goods, or services. The specific embodiments discussed herein are merely illustrative of specific ways to make and use the disclosure and do not delimit the scope of the disclosure.

All publications and patent applications mentioned in the specification are indicative of the level of skill of those skilled in the art to which this disclosure pertains. All publications and patent applications are herein incorporated by reference to the same extent as if each individual publication or patent application was specifically and individually indicated to be incorporated by reference.

The present invention will now be described more fully hereinafter with reference to the accompanying drawings, which form a part hereof, and which show, by way of illustration, specific example embodiments. Subject matter may, however, be embodied in a variety of different forms and, therefore, covered or claimed subject matter is intended to be construed as not being limited to any example embodiments set forth herein; example embodiments are provided merely to be illustrative. Likewise, a reasonably broad scope for claimed or covered subject matter is intended. Among other things, for example, subject matter may be embodied as methods, devices, components, or systems. The following detailed description is, therefore, not intended to be taken in a limiting sense.

Throughout the specification and claims, terms may have nuanced meanings suggested or implied in context beyond an explicitly stated meaning. Likewise, the phrase "in one embodiment" as used herein does not necessarily refer to the same embodiment and the phrase "in another embodiment" as used herein does not necessarily refer to a different embodiment. It is intended, for example, that claimed subject matter include combinations of example embodiments in whole or in part.

In general, terminology may be understood at least in part from usage in context. For example, terms, such as "and", "or", or "and/or," as used herein may include a variety of meanings that may depend at least in part upon the context in which such terms are used. Typically, "or" if used to associate a list, such as A, B or C, is intended to mean A, B, and C, here used in the inclusive sense, as well as A, B or C, here used in the exclusive sense. In addition, the term "one or more" as used herein, depending at least in part upon context, may be used to describe any feature, structure, or characteristic in a singular sense or may be used to describe combinations of features, structures or characteristics in a plural sense. Similarly, terms, such as "a," "an," or "the," again, may be understood to convey a singular usage or to convey a plural usage, depending at least in part upon context. In addition, the term "based on" may be understood as not necessarily intended to convey an exclusive set of factors and may, instead, allow for existence of additional factors not necessarily expressly described, again, depending at least in part on context.

Embryos start their life in the prenatal period of development of the mother as oogonia in primary or primordial follicles containing the early embryo surrounded by a single layer of granulosa cells in the parenchyma of the ovary. The number of follicles found in the ovary during this time period is the highest number the female will have in her entire life and will slowly decrease, mainly due to atresia, for the rest of her lifetime, until exhausted at menopause. During this developmental time period, the oogonia will begin the meiosis process and chromosomal rearrangements that will eventually lead to a genetically unique oocyte. This process will become quiescent during the dictate phase of prophase one and remain there until after birth. At a point in the future further development will begin again. At that time, the granulosa cells that surround the primordial follicle will begin to proliferate and create multiple layers around the oocyte (2-3), at this stage of development structure is called a secondary follicle. This can happen independently of a hormonal influence but further development will stall in the absence of the appropriate hormone cascade. In the presence of hormones a low percentage of follicles will eventually develop a large fluid filled cavity (antrum), 0.2-0.3 mm in rodents and 2-5 mm in humans, and be classified as tertiary follicles.

In humans under normal conditions, a single follicle will fully enlarge and ovulate (termed a graafian follicle) and it is the one that will ovulate. The ovulated oocyte is then caught by the infundibulum and moved into the oviduct for potential fertilization. At this stage of development the oocyte's anatomy has a nucleus, which has reactivated from the dictyate stage of prophase I and is continuing meiosis. The nucleus is housed within a large (>100-um diameter) cell surrounded by the vitelline membrane. Just beneath the membrane are collections of cortical granules. The vitelline membrane is surrounded by a periviteline space, which should contain the first set of cast off chromosomes; the first polar body. A protective protein shell called the zona pellucida surrounds the whole of the oocyte. In mammals, the zona pellucida is a barrier which acts to prevent more than one sperm from entering the oocyte, although it is comment for multiple sperm to appear in the perivitelline space after fertilization. Under normal conditions, sperm cells will use enzymes like esterase, acrosin, and neuraminidase released from its acrosomal region to cause a lysis of the zona pellucida allowing a path into the oocyte. The zona reaction is initiated when the head of the sperm cell fuses with the vitelline membrane. The cortical granules will then fuse with the vitelline membrane and empty their contents into the perivitelline space of the oocyte. This process by the cortical granules is what is thought to be responsible for the zona reaction. Once a sperm cell has successfully crossed the vitelline membrane, the zona pellucida will undergo the "zona reaction" a configurational change in its proteins which will prevent sperm from penetrating, ensuring polyspermia (fertilization of an oocyte by more than one sperm) does not occur.

Once fusion of the oocyte and sperm's membranes complete the sperm cell's head and tail will travel in to the oocyte cytoplasm. The complete penetration of the sperm cell into the cytoplasm activates the second meiotic division of the oocyte, creating a second polar body and allowing for the nucleus to become the female pronucleus. The nucleus of the sperm cell begins to enlarge to form the male pronucleus as the sperm's tail degenerates. The presence of these two pronuclei demonstrates that a successful fertilization has occurred. The male and female pronuclei then will fuse into a single diploid aggregation of the chromosomes creating a zygote.

Once the process of fertilization is complete, the zygote will undergo cleavage. Cleavage is a process of mitotic cell divisions within the zona pellucida resulting in added cell numbers but no growth in size. The cells undergoing cleavage are called blastomeres. The initial one cell zygote will mitotically divide resulting in a two-cell (two blastomere) embryo. Then it will continue to divide creating a four, eight, sixteen-cell embryo and eventually enter into the uterus. With each blastomere division or cleavage, the resulting in smaller cells with less cytoplasm. At this stage the blastomeres begin to tightly align themselves with one another increasing cell-to-cell adhesion, creating a structured complex referred to as a morula. The morula will continue to compact with gap junctions forming between the interior cells and tight gap junctions forming between the cells on the exterior of the embryo. During the next few days fluid from the uterus will begin to seep into the embryo creating a fluid filled cavity called a blastocele. As the cavity fills with more fluid, the individual blastomeres are pushed outward onto the inner lining of the zona pellucida creating a blastocyst. Some differentiation occurs with the cells, some will become the outer cell mass that lines the epithelial wall called a trophoblast, which will become the placenta, and some will group together at the polar end of the blastocyst forming an inner cell mass or embryoblast, which will become the embryo. As the blastocyst expands and grows it will press against the zona pellucida. This pressure, coupled with the release of proteolytic enzymes from the blastomeres, will cause the zona to thin and eventually break, allowing the embryo to be released. This is termed hatching. After the blastocyst has hatched, the trophoblast will associate and establish a relationship with the uterus and implant to gain the necessary source of nutrients for growth.

Developmentally, not all embryos are created equally. A number of different factors that distinguish a high quality embryo from a low quality embryo. Currently, embryos are scored on a variety of factors: Cleavage kinetics, cell number and size of blastomeres, extent of fragmentation, spatial orientation of blastomeres, nuclear status, and degree of compaction for morula stage embryos. Cleavage kinetics represents the speed at which blastomeres within the embryo divide. Although still open to some debate, the thought within the field is that embryos, whose blastomeres cleave at a more hastened pace, within an expected range, are more likely to implant within the uterus. Additionally, the slight increase in cleavage kinetics has been described as a potential marker for the embryo to be euploid as compared to the slower cleaving embryos or embryos developing more rapidly than the expected range. In humans, the ideal timing for embryo cleaving has been shown to be: day one—zygote stage, day two—a two-to-four cell embryo, day 3—an eight-cell, day four—at morula stage and by day 5—a blastocyst. Previous research has shown the transfer of eight-cell embryos on day 3 results in increased pregnancy rates when compared to transfer of slower cleaving embryos with five or fewer blastomeres.

The perfect cleavage occurs when the individual blastomeres within the embryo undergo even division with no fragmentation occurring. Uneven blastomere cell division can lead to three- or five-cell embryos or fragmentation and can be related to irregular nucleokinesis because of potential multinucleation and chromosomal abnormalities. Fragmentation is an anuclear membrane-bound cytoplasmic structures found within the extracellular spaces between blastomeres. These abnormalities result in lower quality embryos and a lower chance of implantation. Regular cytokinesis results in blastomeres of even size and shape with no fragmentations, leading to the ideal blastomeres.

Spatial orientation of the blastomeres is the next factor to be considered when looking at overall quality of the embryo. The first cleavage plane in mammalian embryos should be straight through the axis of the embryo, this should result in two even-sized daughter cells. The second cell division is the same as the first resulting in 4 even daughter cells. The third cleavage plane is equatorial, resulting in an embryo that has a tetrahedral appearance. Embryos that don't have this type of division can result in a disturbance of animal and vegetal cytoplasm creating a potentially lower quality embryo.

Nuclear status of the embryo is just as important as cleavage rate and spatial arrangement of the blastomeres. Two or more nuclei per blastomere (multinucleation of the embryo) can be potentially problematic. This can be difficult to observe because normally embryos are observed on a daily basis at one time so this problem can be underreported. Multinucleation can occur from a variety of problems: karyokinesis in the absence of cytokineses, partial fragmentation of the nuclei, or a potential error in chromosome separation. Multinucleation has been shown to result in cells with abnormal chromosomal numbers and a potential for a high error rate in the embryos chromosome quality.

The final characteristic that can give an idea of embryo quality is the degree of compaction within the morula stage embryo (16-32 blastomeres). Tight gap junctions form between the blastomeres causing the individual blastomeres to be more difficult to distinguish from each other. These gap junctions allow the embryo the ability to create an inner cell mass and develop further. A lack of compaction or only a partial compaction (less than half of the blastomeres show compaction) results in embryos with little to no developmental potential.

As described above, to date embryo assessment in IVF programs has been based on multiple factors when looking at the embryo which include: Cleavage kinetics, cell number and size of blastomeres, extent of fragmentation, spatial orientation of blastomeres, nuclear status, and degree of compaction for morula stage embryos. While these methods have proven useful and resulted in higher pregnancy rate, none have led to the targeted golden standard of IVF; one embryo developing into one pregnancy, with one baby born every single IVF transfer attempt.

Assisted Reproductive Technologies (ARTs) have made significant improvements over the last thirty years. Improvements in management protocols, culture technique, and culture media have helped increase pregnancy rates while simultaneously decreasing the number of embryos transferred. Programs which once measured success rates in terms of the occasional pregnancy now routinely report annual success rates 40%-60%. The ultimate goal of all ART programs should be to move toward single embryo transfers while maintaining high pregnancy rates. However, this requires the ability to select those embryos with the greatest potential for implantation and development. Two issues remain problematic for ART; 1) multiple gestations and 2) the fecundability of individual embryos. Traditionally, embryos have been selected solely on their morphologic appearance and normal rate of development. The current recognized laboratory standard for determining which embryos will be transferred is morphological appearance. However, data from a recent Proficiency Testing Survey from the American Association of Bioanalysts suggests there remains significant disagreement among labs as to what constitutes a "normal embryo." Fully one-quarter of the labs participating in the survey disagreed on the quality of embryos used in the evaluation.

Given the cost of the procedures, risks associated with medications and surgical procedures, and the emotional toll negative pregnancy results have on the couple; any improvement in embryo selection which; non-invasive, less subjective and leads to higher pregnancy rates, while limiting the risk of multiple gestations would represent a significant improvement in women's reproductive health.

The use of pre-implantation genetic diagnosis/pre-implantation genetic screening (PGD/PGS) has proven a significant step forward in in the selection process. However the procedure is invasive, not without risks, and can sometimes lead to erroneous results. It is also time consuming and requires a significant investment in equipment. Further, by the very nature of the test, it only tests the genetic fitness of the embryo, revealing little about the embryo's other physiological processes. Numerous groups have been searching for a non-invasive means of improving embryo selection which would provide a complete picture of the embryo's ability to implant and develop. However, to date, little progress has been made in finding an alternative to traditional morphology alone or morphology coupled with PGD/PGS.

While genetic composition is crucial to normal embryo development, it must be recognized that embryo development requires a number of factors, including an energy reserve and necessary chemical processes to survive from fertilization to implantation. The present invention presents a novel, non-invasive technique to potentially assess these factors which can be applied at the earliest stage of development. In one embodiment, the present invention considers that given the consistent shape and size of an oocyte and/or early embryo at the same stage of development and the fact that all other parameters would be equal in an in vitro culture system, any differences seen in embryo weight (density) should be the result of differences in internal embryo chemistry, which would be expected to influence embryo viability. In one embodiment, the present invention comprises a system for estimating the weight of an embryo based on specific gravity. Using the system of the present invention, cryopreserved cattle blastocysts from animals with known differences in body composition, primarily intramuscular deposition, demonstrated differences in density, these differences are due to lipid content within the embryos. Further testing with fresh mice embryos confirm this observation, both using mouse strains of different maternal weights and a single strain with animals of different weights. However, in both of these studies there were embryos with weights significantly higher or lower than the establish population mean (i.e., >+/−2 STDs from the mean).

It was found that light weight (long descent time) embryos fail to develop at a significantly higher rate compared to the rest of the cohort. Earlier work, suggests these differences are mainly due to a large incorporation of lipids into the embryo cytoplasm. Previous studies have suggested that changes in the embryonic cytoplasm as well as chromosomal anomalies account for most of the issues with embryonic growth. It is clear that the system, which is easy to use, presents little to no risk to further development and allows 100% recovery of embryos and can detect differences in growth potential at the earliest stages of development. Further study, with a significantly larger embryo cohort, is ongoing, including expanded biochemical analysis. An unexpected finding from the study was the increased number of embryos that developed to blastocyst after being in the device of the present invention versus the number that developed in the culture-only control.

Advancement in all aspects of ART has improved the technique to the point where both researchers and lawmakers are calling for single embryo transfer to become the norm. Because PGD/PGS, which is limited to detecting chromosomal abnormalities, and simple morphology, for which the usefulness in SET continues to be debated cannot ensure continued development of embryos post-transfer, there remains a need for improved selection criteria before mandating SET. The device of the present invention, by itself, or in combination with other techniques, might represent a step forward in determining individual embryo fecundity and embryo selection for SET.

It is therefore an embodiment of the present invention to provide a system for the non-invasive grading of early stage embryos (pre-hatching) based upon specific gravity, density and/or estimated weight. In one embodiment the system allows 100% recovery of embryos and can detect differences in growth potential at the earliest stages of development. Estimation of embryo weight is a measure to help better determine biochemical composition of the embryo as an objective way of determining embryo viability. Potentially knowing the relative concentration of each biochemical constituent in the embryo could suggest which embryo will be viable and lead to a successful pregnancy. Estimation of embryo weight is obtained by a modified specific gravity technique, which has been a common means of estimating lipid content in live individuals and food products. Specific gravity determination involves water displacement that helps determine the density of the embryo. As differences in weights of objects of equal size are based solely on density, the density of the embryo at this stage of development must be an estimation of weight. The weight of the embryos differs between breeds, which appears to be the result of differing lipid content. In a study in cattle, Jersey cattle embryos contained significantly more lipids than beef cattle embryos leading to overall lighter weight embryos. In a follow-up study, mice embryonic weight was shown to correlate with maternal body composition and possibly a correlation between embryo weight and development. Therefore, estimating the embryo weight might lead to an estimation of embryo biochemical composition and suggest a better selection of viable embryos for in vitro fertilization.

The study of flow chemistry is the study of chemical reaction in a flowing stream instead of a static batch production. A micro fluidic device can be described as a tube or channel that has either a constant flow of some fluid streaming through it at a certain velocity. A segmented flow system where there is gaseous bubbles or solvent spacers to separate specific reactions or materials from one another can be used as well. Such systems have been proven to have many benefits such as an excellent heat and mass transfer capability, allowing for tight temperature control at exponentially high or low temperatures for increased reaction rates. Micro fluidic devices have also shown to have elastic instabilities that allow for induced diffusion between whatever fluid is in the device and the particle, reaction or material traveling through it.

Microfluidics and the study of embryos has been a new use in recent years. Studies of Drosophilia embryonic patterning have been studied where the anterior side of the embryo has been exposed to one temperature while the posterior side is exposed to another to see the different rates of development due to the different temperatures. Further, the formation of left-right asymmetry in the vertebrate has been studied using mice embryos and a micro fluidic device. However, to date few, if any, studies have explored the possible role of microfluidics in early embryo culture.

In one embodiment the present invention presents a specific gravity means of assessing embryo weight. While not a true microfluidic environment, in that the embryo travels through the fluid rather than fluid flowing over the embryo, presenting microfluidic effects on the embryo as it descends through the specific gravity chamber and simultaneously providing benefits to embryo culture, which enhances growth and/or development.

In another embodiment, the system is composed of a drop chamber, referred to as the tube, extending into to a collection pool, referred to also as the collection pool, to allow for recovery of embryos. In a further embodiment, the system contains, and is operated using, an embryo culture media of users choosing and compatible with embryo survival outside of controlled culture conditions. In an even further embodiment, the system contains, and is operated using, an embryo culture which is a growth supportive embryo culture media (i.e. culture media which actually enhances embryo growth).

In yet another embodiment, the system contains a pressure seal to allow the media to be continuous from the top of the drop chamber to collection pool. The system has a "timing zone" to determine the descent time of the embryo over a known distance. The timing zone may be designated by marks, etching, pigments or inks, or other methods to designate the upper and lower boundaries of the timing zones. The tube which comprises the lumen acting as the drop chamber is preferably transparent, or is comprised of sections related to the applicable timing zone to allow for detection and assessment of the descent of the embryo of interest. In a further embodiment, assessment means any observation or evaluation through visual means or by other means of detecting the movement downward of the embryo of interest, including assessment by tagging, markers, or by computerized means utilizing a processor having programmable logic designed to detect the embryo of interest during descent through the timing zone.

In a further embodiment the system drains media from the drop chamber into the recovery collection pool upon breaking of the pressure seal to ensure flushing of the embryo into the recovery collection pool, thus creating fluid communication between the lumen of the tube and the collection pool. It is a preferred embodiment of the present invention that said system potentially increases the embryo growth rate over static culture.

In yet another embodiment, the system has an optional rotating, revolving, carousel, or otherwise multiple-welled or multiple-strawed configuration, allowing for the ability of the drop chamber (the tube) to have multiple chambers, each having its own collection pool, or collection pool to allow collection of information about individual embryos. In another embodiment, the a single drop chamber (the tube) is positioned at various times over multiple collection pools to allow collection of information about individual embryos while allowing a single chamber's use.

Turning to the figures of the present invention, various aspects are described. FIG. 1A depicts the specific gravity system as designed for use (note lid has been removed from diagram for ease of visualization). A tube 102 is positioned above a collection pool or reservoir 104. The outer diameter of the tube 102 allows for monitoring of the inner lumen 101 which acts as a descent chamber of the tube 102. Culture media which is biocompatible is maintained in the inner lumen 101, as well as in the collection pool 103. The tube 102 is positioned vertically over the collection pool 103 in order for the lower end of the tube 105 to allow fluid communication to exist between the lumen 101 of the tube 102 and the collection pool 103. An outer surface of the collection pool 104 is designed to contain the culture media. The configuration of the collection pool may be cylindrical, rectangular, or any shape necessary for compatibility with surrounding equipment and instrumentation. An embryo is placed at the top of the open end of the tube, the lumen 101 representing a specific gravity chamber and allowed to sink through the media. The embryo is then subjected to assessment. In one embodiment, the embryo's rate of descent is measured as it passes through a marked, or otherwise distinguishable, section of the tube labeled the "timing zone." For example, the timing zone may be 10 cm in the length or less. In one embodiment, the timing zone is 5 cm. In another embodiment, the timing zone is 2 cm. In a preferred embodiment the timing zone is 1 cm. Once the timing is completed the embryo continues to descend into the middle section of a collection pool, which may represent a standard organ culture dish or other reservoir capable of receiving the embryo within the culture media, which may be biocompatible in one embodiment, and growth supportive in another embodiment.

Turning to FIG. 1B, a representative device of the present invention is shown with a lid configuration 106 and positioned horizontally, which is non-functional in terms of performing assessments of embryos. The lid 106 allows for protection and pressurization of the inner collection pool housed by the outer portion of the collection pool 104. The lumen 101 is presented within the tube 102, which extends distally from the collection pool 104. An aperture 107 in the lid 106 is capable of receiving the tube 102 for purposes of insertion into the collection pool 104 and achievement of fluid communication between the lumen 101 and the inner collection pool 104. For the purposes of the present invention the device must be positioned vertically for the assessment to occur, as the descent of an embryo may be affected by positioning the tube 102 in any position that is not vertical. The lid 106 can then be removed for easy embryo recovery and return to culture.

Figure 2:
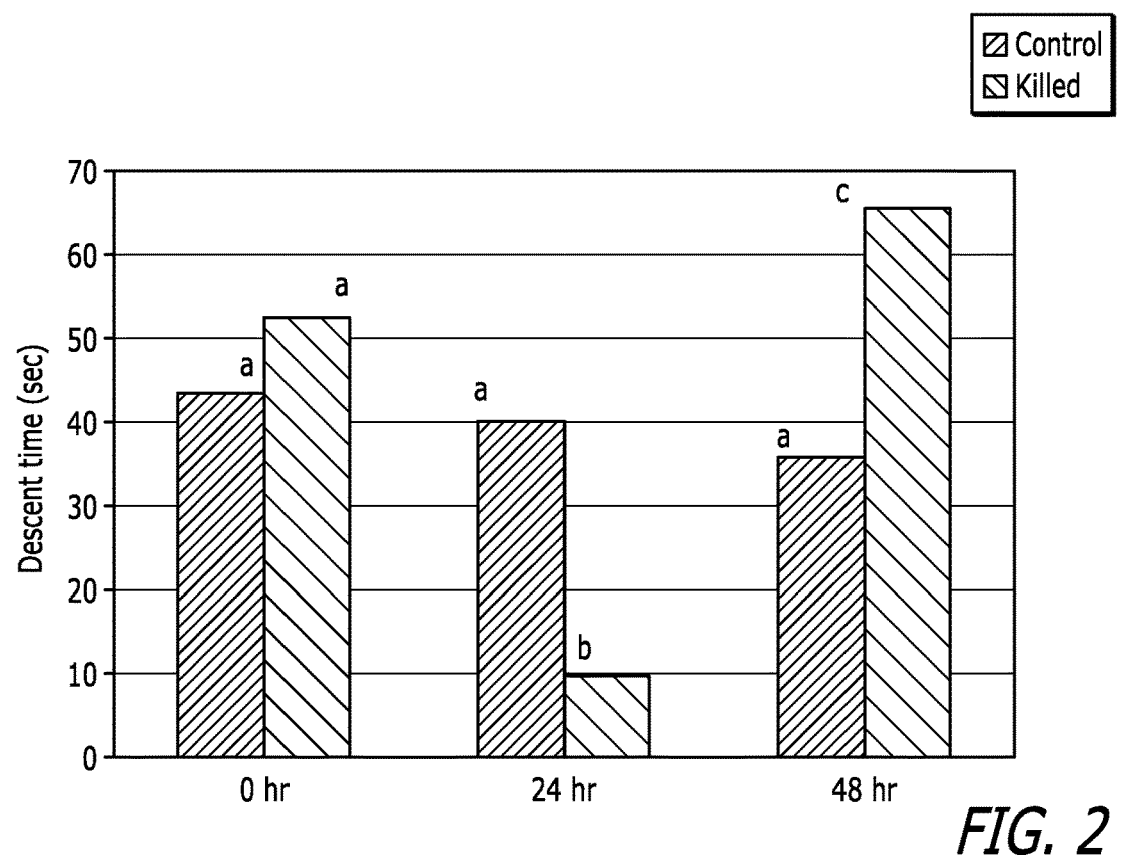
FIG. 2 depicts a comparison of the descent time of control (non-heat exposed) and heat-killed embryos through the system of the present invention at 24 hour intervals over a two day period.

FIG. 2 presents a comparison of the descent time of control (non-heat exposed) and heat-killed embryos through the device of the present invention at 24-hour intervals over a two-day period. While the control embryos demonstrated patterns similar to those reported in previous studies, heat-killed embryos exhibited drastically different patterns of descent. The expectation that the differing patterns of descent are attributable to changes in membrane integrity ($P<0.001$).

Figure 3:
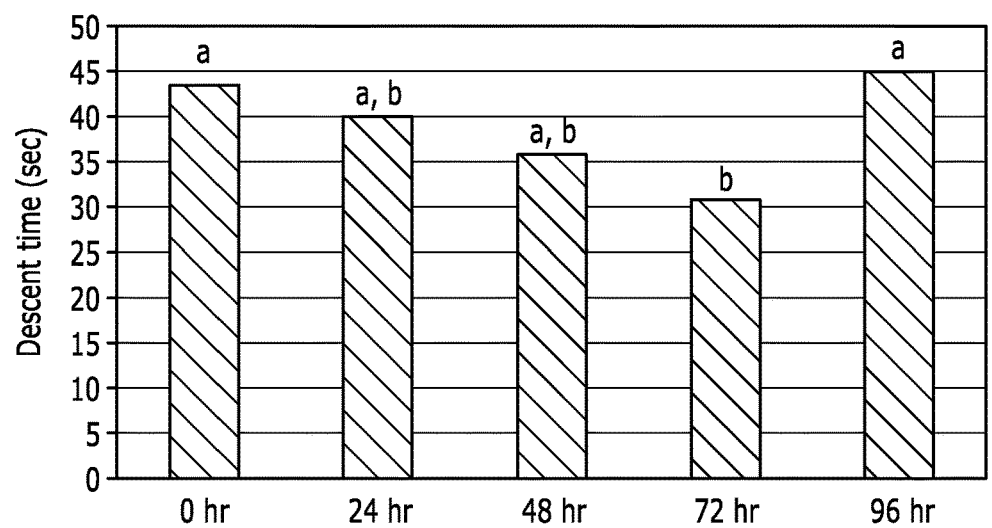
FIG. 3 depicts descent time of control (non-heat exposed) embryos over a five day period through the system of the present invention.

FIG. 3 presents the descent time within the device of the present invention of control (non-heat exposed) embryos over a five-day period. Note changes in descent time appear to be affected by increases in embryo cell number as embryos continue to grow over time (time 0 hour—one cell stage, 96 hours—blastocyst). Bars with different letters indicate a difference between measurement times ($P<0.02$).

Figure 4:
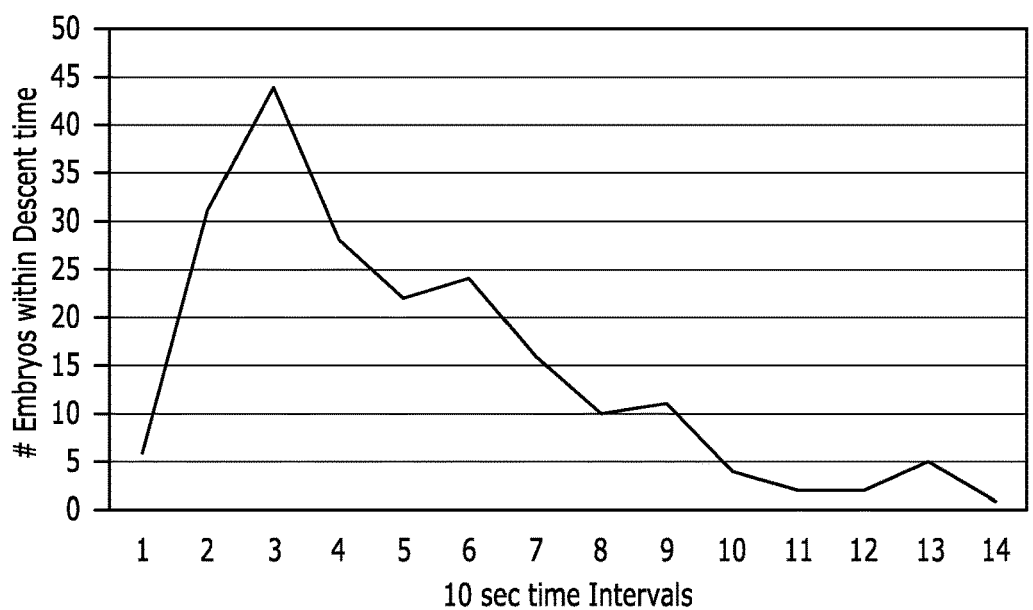
FIG. 4 depicts a comparison of the descent times of 207 one-cell embryos from 27 donor animals "dropped" through the system of the present invention.

FIG. 4 presents a comparison of the descent times of 207 one-cell embryos from 27 donor animals "dropped" through a the device of the present invention, which acts as a modified specific gravity chamber. While descent times ranged from 10-140 seconds, >70% of the embryos was clustered+20 seconds of the population mean. Furthermore, the data for individual embryos suggest a skewing towards faster descent times, attributable in part to the influence of maternal body composition.

Figure 5:
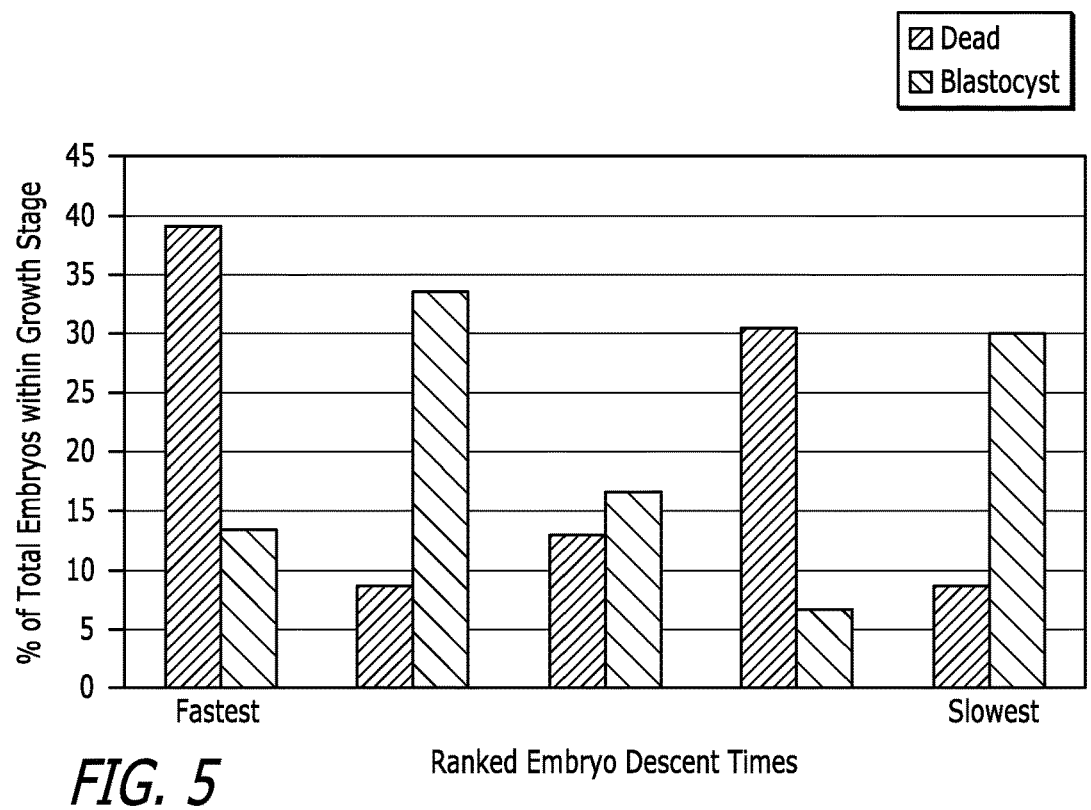
FIG. 5 depicts a relative weight comparison using a modified specific gravity chamber represented by the device of the present invention (faster descent time=heavier weight) of all embryos from 27 animals which either stalled or died at the one-cell stage compared to those that reached the blastocyst stage after 4 days in culture.

FIG. 5 presents a relative weight comparison using the device of the present invention which serves as a modified specific gravity chamber (faster descent time=heavier weight) of all embryos from 27 animals which either stalled or died at the one-cell stage compared to those that reached the blastocyst stage after 4 days in culture. Embryos which developed to blastocyst tended to have median descent times while those that stalled tended to have descent times at the extremes ($P<0.001$).

Figure 6:
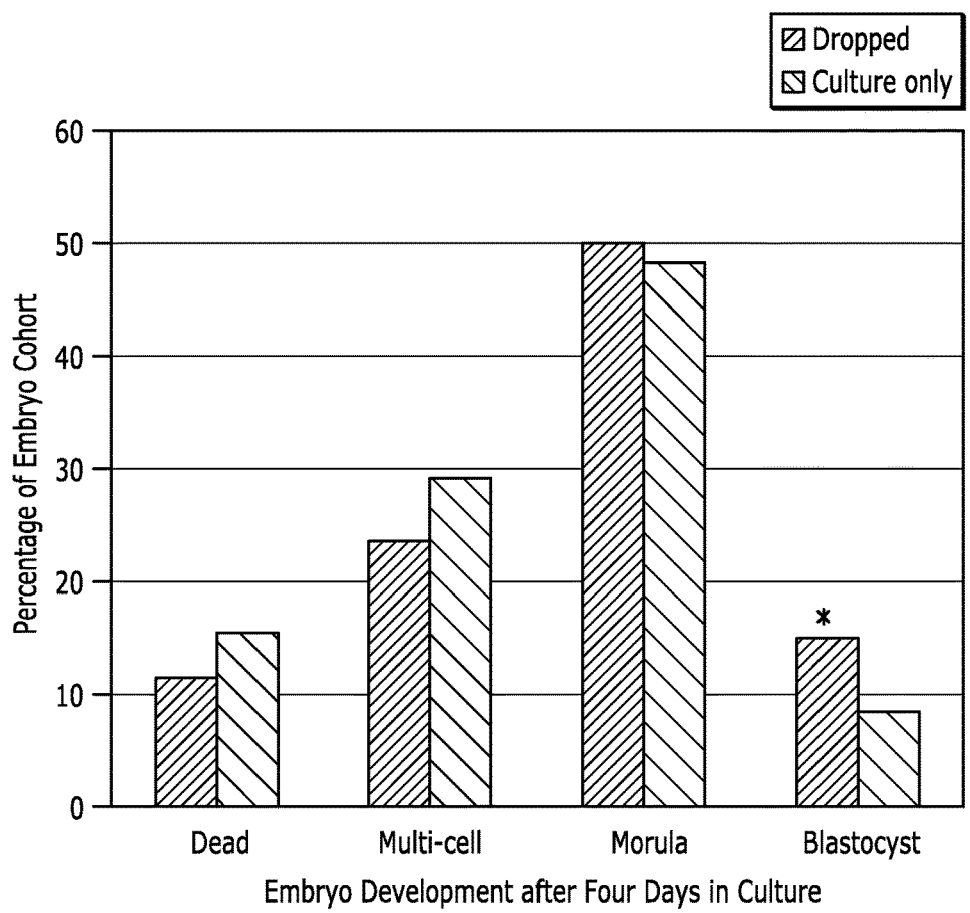
FIG. 6 depicts a comparison of the growth patterns of mouse embryos over a four day period for embryos which had been first passed through the device of the present invention to estimate their zygotic weight (N=207) versus those placed directly into culture (N=207).

FIG. 6 presents a comparison of the growth patterns of mouse embryos over a four day period for embryos which had been first passed through the device of the present invention to estimate their zygotic weight (N=207) versus those placed directly into culture (N=207). Data suggest a higher rate of blastocyst development in embryos exposed to the device of the present invention ($P<0.01$).

Those skilled in the art will recognize that the methods and systems of the present invention may be implemented in many manners and as such are not to be limited by the foregoing exemplary embodiments and examples. Furthermore, the embodiments of methods presented and described as flowcharts in this disclosure are provided by way of example in order to provide a more complete understanding of the technology. The disclosed methods are not limited to the operations and logical flow presented herein. Alternative embodiments are contemplated in which the order of the various operations is altered and in which sub-operations described as being part of a larger operation are performed independently.

The examples below provide illustrative embodiments of the present invention. While various embodiments have been described for purposes of this disclosure, such embodiments should not be deemed to limit the teaching of this disclosure to those embodiments. Various changes and modifications may be made to the elements and operations described above to obtain a result that remains within the scope of the systems and processes described in this disclosure.

Example 1: Design of Specific Gravity Chamber for System

Initial studies were conducted using 0.5 mL straws filled completely with media. The media-filled straw, serving as the tube, was positioned perpendicular to the ground such that the open end was at the top and embryos were placed at the meniscus and allowed to descend in response to gravity while being observed through a dissecting microscope. While it is recognized that specific gravity techniques measure density, in cases where the object's shape and size are equal density is a very close estimation of weight. Therefore, by measuring the descent time of the embryos over a set distance and comparing it to the descent time of beads of a similar size and shape to embryos, and with a known weight of the beads, a mathematical formula was derived making it possible to estimate embryo weight as shown in more detail below.

The system of the present invention allows the embryo to complete its descent into the central well of an organ culture dish. The lid of the dish is modified to accommodate the descent chamber, by providing an aperture in the lid for insertion of the tube, and is also equipped with a pressure seal to maintain the fluid levels within the descent chamber during use. Prior to testing embryos, the established mathematical formula was verified using previous experiments with bead controls. One hundred percent of the beads were recovered in the lower central well. Once the standard curve was re-established, a series of one-cell embryos (N=35) were collected from 4 mice (CB6F1 mice; Charles Rivers, Burlington, Mass.) previously stimulated using standard protocols, were run through the chamber to test recovery. It was found that most embryos were automatically located in the lower central well. It was also found that the few embryos that adhered to the wall of the descent chamber could be rinsed into the central well and 100% of embryos "dropped" through the system were recovered. Embryos were then placed in culture to determine whether they would continue development for a minimum of two division cycles.

Distinguishing Between Live and Dead One-Cell Embryos

It is well established that living cells are dependent on their semi-permeable membranes to establish the chemistry necessary to sustain life. The destruction of the semi-permeable properties of the membrane would cause leakage of cellular components, changes in intracellular chemistry and, therefore, in theory, a significant shift in cellular weight as water shifts into and out of the cells. Using this approach, the device of the present invention is capable of detecting differences between living and dead embryos based on changes in embryo's specific gravity after death. To prove this hypothesis, embryos were collected from a series of 5 mice (N=79) after hyperstimulation. The embryos from each mouse were split equally between two treatments. The first group of embryos (N=39) were weighed and then placed into standard culture using 10% serum and a Ham's F-10 media (Irvine Scientific; Santa Ana, Calif.) for a period of 48 hrs. The second group of embryos (N=39) were also weighed to insure consistency with the first group's initial assessment, but then killed by placing their culture dish on a 60° C. hotplate for 30 minutes. Once heat killed, these embryos were placed under the same culture conditions as the controls. All embryos were re-weighed using the device of the present invention after 24 and 48 hrs in culture and controls weighed every 24 hrs after until 120 hours (see FIG. 2).

Weight of One-Cell Embryos Versus Future Growth Pattern

Once it was determined that the device of the present invention could determine differences in embryos with known differences in cellular content resulting from changes in membrane permeability (live versus dead), a series of animals (N=27) were stimulated as above to create one-cell embryos. Since it was known from previous experimentation that maternal body composition can influence embryo weight, no more than 20 embryos (ten for each experimental arm of the study) were used from any single mouse. Half the embryos (N=207) were placed directly into culture as described above and assessed for development daily. The remaining half (N=207) were first weighed and then placed into culture. All embryos were assessed for development daily for a four day culture period. At the end of the culture period, embryos were ranked from 1-4 for final development (1=remain 1 cell or died, 2=multicell, 3=morula and 4=blastocyst) and compared to the initial weight estimate to determine any relationship between initial weight and final growth potential.

Statistical Analysis

All data were analyzed using the Statistical Package for the Social Sciences (SPSS ver. 12; Chicago, Ill.). The basic analysis was a two-way analysis of variance of treatment by time using a p-value of 0.05 for significance. In cases of significance by the original analysis, differences within time or treatment were re-analyzed with either Student's t or one-way analysis of variance with Tukey's mean separation as appropriate.

As described above, it is recognized that specific gravity is a measure of density, not weight. However, if the shape and size of the objects being measured are held constant, then density becomes a good estimation of weight. Given the consistent size and shape of most non-expanded embryos (zygote to early blastocyst stage) the device of the present invention should provide an estimation of weight. Initial studies show the device of the present invention containing a collection pool within a chamber not only demonstrated 100% recovery of embryos, but also that the recovered embryos continued to develop at normal rates through 2-4 division cycles. Further, as the chamber media had not changed and repeated measurement of the descent times of the control borosilicate glass beads (data not shown) were similar to measurements performed in the previous chamber, the same curve could be used to estimate embryo weight. As suggested by previous work, it appeared weight might be a useful tool in predicting embryo growth and justified future investigation of early embryo weight's relationship with embryonic development.

Once the ability to recover embryos and weight curve were verified using the redesigned chamber, experiments were conducted to determine the weight differences between live and dead embryos. In these studies, groups of embryos were killed by exposing their culture environment to an extreme heat load (60° C.) for a period of 30 minutes. A small group of embryos were then stained with a vital dye to confirm loss of membrane function. The remaining killed embryos and a non-heat exposed group (control) were then weighed daily at 0, 24 and 48 hrs, and the control for two additional days. As expected, all embryos demonstrated similar descent times (and therefore weights) at the 0 time point (See FIG. 4). Further, embryos in the control group demonstrated increasing weights (decreasing descent time) as they progressed from the one-cell stage to multicellular structure, and then a decrease (increased descent time) as they developed a blastocoel cavity (See FIG. 5; $P<0.02$). However, the killed embryos demonstrated significant shifts in descent time over the 48 hr period (See FIG. 2; $P<0.001$); first demonstrating a significant decrease in descent time at 24 hrs, potentially as the dead membranes allowed significant movement of water into the cells in response to cytoplasmic constituents, and then a significant increase in descent time as the dead cells leaked cytoplasmic elements due to simple diffusion and established almost perfect equilibrium within the media environment. It is recognized that the latter is a poor estimation of embryo weight due to similarity of the specific gravity of the media and embryo causing the embryo to "float" in suspension, rather than descending. However, the difference in descent time remains a good indicator of embryo growth potential.

Given the ability of the system to detect differences between live and dead embryos, the final experiment attempted to determine if estimated weight (or descent time) of zygotes correlated with later development. A total of 414 mice embryos were used. Half were placed directly into standard embryo culture and half were evaluated with the device of the present invention as zygotes (single time) prior to culture. All embryos were then monitored individually and on a daily basis for development over four days. Embryos that became discolored or had obvious degeneration of blastomeres were deemed to have died in culture.

While the descent times of the cohort of embryos from a single animal tended to form a bell shaped curve around the mean, the descent times for all 207 embryos formed a skewed curve due to the previously suggested influence of the maternal donor Therefore, to allow a comparison between animals, all embryos from a single animal were ranked from slowest (lightest weight) to fastest (heaviest weight) based on rates of descent through the inner chamber within the lumen of the device of the present invention. Sixty-five percent of the embryos developed to morula or blastocyst over the four day culture period, with 12% developing to a multi-cell stage (4-16 cells) and 13% remaining as one cell or meeting the criteria of death. While there were embryos of all weight ranks represented in each stage of development, the vast majority of the embryos with the longest and shortest descent times were embryos found to have died in culture. Further, comparing this group to the embryos that developed to blastocyst suggested that while the embryos that developed to blastocyst demonstrated the same bell-shaped curve of the population as a whole, the embryos that died in culture generated a U-shaped curve (see FIG. 6; $P<0.001$). These findings suggest there may be differences in the embryo constituents at zygote formation which will lead some to develop and others to stall or die.

Finally, growth rates of embryos passed through the device of the present invention were compared to growth rates of the embryos placed directly into culture. Both groups demonstrated >50% development to the morula and blastocyst stages after four days of culture. However, embryos passed through the device of the present invention demonstrated greater development to blastocyst during the culture period.

Example 2: Prediction of Embryo Rates and Pregnancy Outcomes

Example 2 describes the ability of the present invention to determine differences in weight in order to sort embryos. One issue requiring resolution is to reduce loss of embryos in the system, which in many instances, including human application, the present invention requires virtually 100% recovery for each set of embryos analyzed. Therefore the objectives of the present example are to: 1) allow easy recover of all embryos; 2) demonstrate the continued growth of the embryos in culture; 3) demonstrate the system distinguishes between live and dead embryos, and 4) sorting viable embryos.

Verification of Specific Gravity Chamber. The embryo specific gravity chamber, presented as the device of the present invention, was designed to facilitate embryo recovery. In order to properly calibrate the chamber for purposes of determining weights of the embryos, 100 beads of 4 different known weights and sizes were dropped into the device and the rate of decent timed over a 1 cm distance. Resulting data was then analyzed for reproducibility. Once reproducibility was confirmed, the mean value of the two beads of either borosilicate or barium-titanite was used to create a standard curve using a curvilinear equation and forcing a zero-time on the X-axis to establish an equation for estimating embryo weight. Crucial to all subsequently planned experiments, after an initial training period, 100% of the beads were recovered following the drop procedure, suggesting that no embryos would be lost as a result of this testing procedure. As expected from previous research, rates of decent for each bead type were highly repeatable varying on average by less than 8%. Using the two-point time for each type bead (Borosilicate and Barium-titanate) a mathematical equation was derived by forcing a time point where time crossed both axis:

Borosilicate: $y=-0.1613 \ln(x)+1.3509$ $R2=0.9108$

Barium-titanate: $y=-0.4379 \ln(x)+0.9714$ $R2=0.9998$

Comparing curves, the Barium-titanate curve established a strongly correlated curvilinear relationship ($R2=0.9998$).

In applying the test to confirm embryo recovery, four mice were stimulated for 1-2 embryo recovery using standard techniques. Recovered embryos were placed in culture for 12 hours prior to experimentation. Embryos were dropped through the system in a fashion similar to the beads and recovery rates were noted. The embryos were placed back in culture to determine progress through at least two division cycles. After an initial training period with glass beads, no beads or embryos were lost during their exposure to the redesigned specific gravity chamber suggesting this is a tool which can be used with human embryos without fear of embryo loss.

In determining whether the embryos are distinguishable between live and dead embryos, cell embryos were divided amongst three treatment groups. The first embryo treatment group was heat killed with a hot plate. The second embryo treatment group was killed with 3% paraformaldehyde. The third embryo treatment group was killed with HCl at pH ~6.8. The weight of the embryos dropped into chamber was recorded after expected death, and weight of dead embryos was determined for 5 days. Studies with purposely killed embryos demonstrated the ability of the system to distinguish between live embryos were able to be differentiated from dead embryos based on differences in specific gravity (weight).

In testing for embryo survival and development, a control set of embryos were cultured and the cell count checked each day. A test group of embryos was dropped with weight recorded daily. The cell count of dropped test group was tested daily. The data suggests that early embryo weight can be used to distinguish between embryos that will develop in culture verses those that will stall or die. These findings are supported by early pregnancy studies. Preliminary data suggests that early embryo weight can be used to distinguish between embryos that will develop in culture verses those that will stall or die. These findings are supported by the early pregnancy studies.

In testing the system's ability to determine growth potential, one-cell embryos were collected and split between control and drop treatments. Controls were placed in culture and evaluated daily for four days. The test group underwent a single weighing on day one, and were then placed in culture for four days. As with the controls, they were evaluated daily for development.

In testing for weight in relationship to pregnancy, frozen sheep embryos were thawed and dropped through the device of the present invention. The embryos were sorted based on weight. Embryos of similar weights were transferred as twins into recipient ewe and pregnancy was determined by DG29 blood test.

Figure 7:
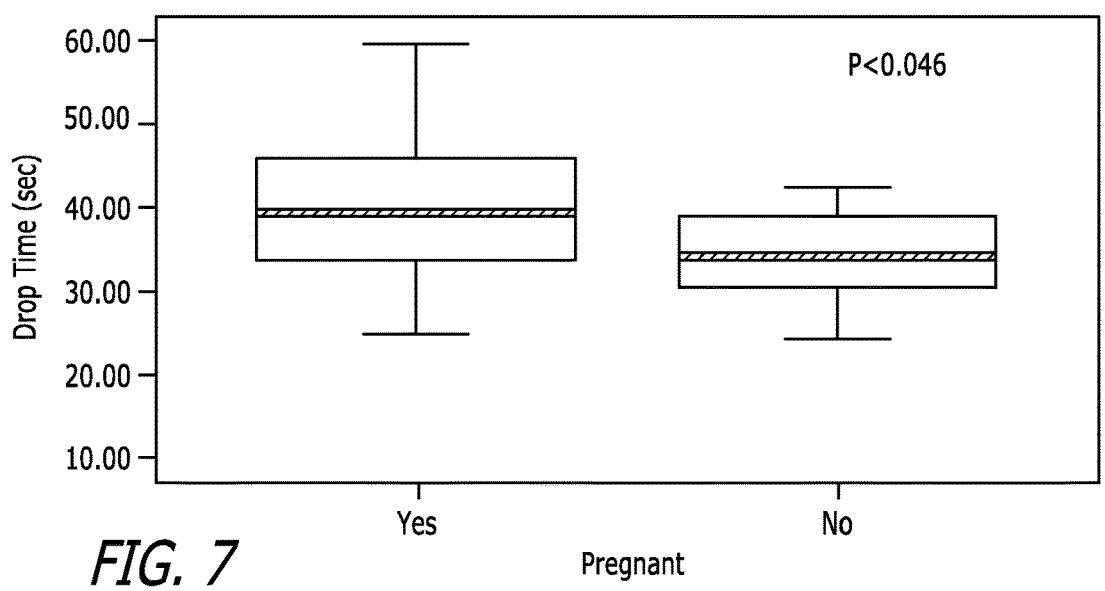
FIG. 7 depicts a comparison of embryo weights of pregnant and non-pregnant ewes which were based on assessment of the system of the present invention.
Figure 8:
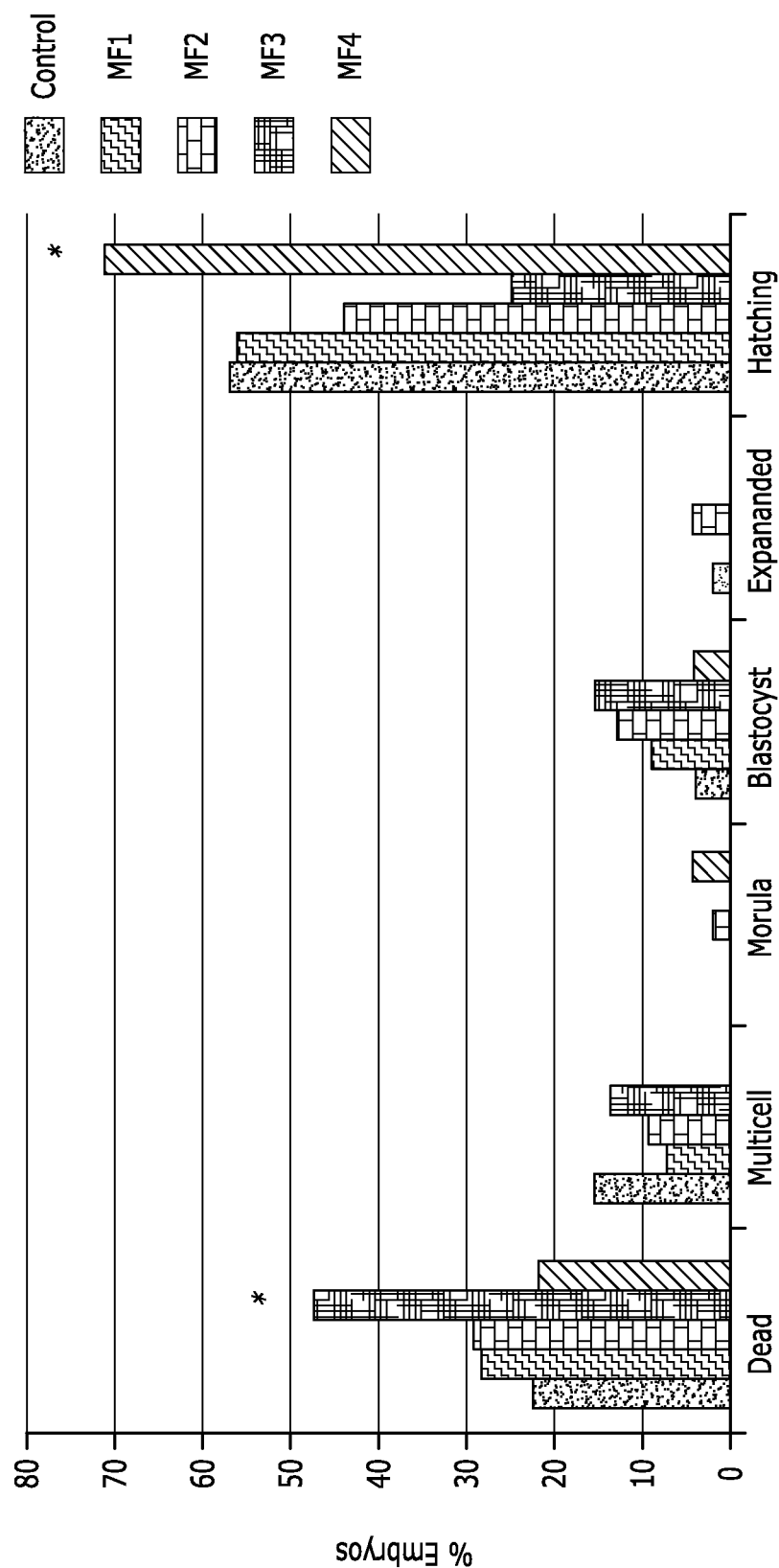
FIG. 8 depicts a comparison of the growth and development of embryos over a five-day period which have been first passed through the device of the present invention having a supportive growth culture media and multiple tubes of differing lengths used for said drop chambers.

From the above example, tests of the redesigned chamber with mice embryos demonstrated a 100% embryo recover rate and a 100% continued development rate for at least two divisions post-weight determination (FIG. 2). The dropped group continued to grow and develop as compared to the control culture group indicating the specific gravity chamber does not inhibit embryo growth or develop (FIG. 5). However, while the viable embryos demonstrated a predictable pattern of descent time (and therefore weights) over the first 48 hours of development, embryos in all three treatment groups demonstrated significantly altered drop patterns (FIG. 6). All "killed" embryos first descending faster as the cell membranes lost their ability to osmoregulate due to membrane damage. However, the heat killed embryos then dropped slower than live embryos slower potential due to loss of materials "leaking" out a of severely damaged membrane and being replaced by the osmotically balanced culture media. The formaldehyde killed embryos continued to be faster than controls at 48-hour time point possibly do to the crosslinking of proteins preventing their escape from the cells. The HCl killed embryos continued to increase in weight over time. This is possibly due to a delay in death as demonstrated by a view embryos going thru one division cycle. Interestingly, in the subsequent experiment were embryos were dropped a single time and them cultured, a significantly higher number of embryos grew to blastocyst that those cultured alone (P<0.01; FIG. 6). Further, about 20% of the embryos dropped at the one cell stage failed to progress and died in culture. Like the earlier heat-killed embryos, they had significantly higher or lower weights that the general cohort of embryos that progressed to blastocyst (P<0.001; FIG. 7). In a separate study with sheep embryos, embryos of lighter weights established pregnancies at a higher frequency than did heavyweight embryos (P<0.046; FIG. 8).

Example 3: Determination of the Relationship Between Length of the Drop Chamber and Embryo Development The push toward single embryo transfer (SET) has created an ever increasing need for high quality embryos. Numerous groups have proposed the use of microfluidics as a means of increasing embryo quality. However, to date, no practical means of creating a microfluidics environment (MFE) has been developed. The system of the present invention provides a Modified Specific Gravity Technique (MSGT) in determining the best embryos for transfer. Results show an improvement in embryo quality due to a momentary exposure to a MFE. The objective of the present example is to show that MSGT enhances embryo development due to momentary exposure to a MFE and the limitation of such treatment. Two-hundred and fifty, single-cell mice embryos were collected and split between five treatment groups designed to produce varying exposures to MFE. The control was standard microdrop culture. The momentary MFE was varied by shortening the drop chamber in the MSGT creating exposure times of between 2-8 minutes. Following exposure to the MFE, all embryos were cultured using the same methods as the control and followed for 5 days to assess development.

As in the previous examples, embryos in the standard MSGT displayed significantly higher rates of hatched blastocyst development compared to the control (70.6% vs 56.6%; P<0.001). This pattern was also seen at the morula and blastocyst stage of development (P<0.011). However, shorter exposure to the MFE appeared to have no, or a detrimental effect on embryo develop compared to the static drop controls (P<0.001). This data continues to suggest that the standard MSGT enhances embryo development through exposure to an MFE.

Example 4. Enhanced Embryo Development

The prior examples present the system of the present invention providing a modified specific gravity technique (MSGT) to establish the utility of the system of the present invention in estimating embryo weight and providing both an estimate of embryo chemical composition and potential viability of embryos. Observations during these studies suggested a microfluidic type effect (MFE) during the embryo weighing process, which appeared to result in improved growth rates [40]. The present experiment was designed to examine the potential micro-fluidic effects of the MSGT and the direct effects different exposure times (and potential different MFE forces) had on embryo development.

The specific gravity device previously described was made using the lid of a standard 60-mm petri dish (Falcon; Union City, Calif.), and a standard 132-mm, transparent 0.50 mL semen straw (Minitube; Tiefenbach, Germany). The development of the initial device was done by first removing the cotton/sand plug from a 0.50-mL semen straw, or tube, and cleaning it thoroughly using ethanol, then rinsing the ethanol off with deionized (D.I.) water. The straws were allowed to dry and marked with 2 lines making a 1-cm length space from line to line; with the start line approximately 5 mm from the top of the straw. A hole large enough to accommodate the straw was placed in the center of the petri dish lid using heat. The hole was made smooth with a round micro file and then cleaned using ethanol and D.I. water. The marked straw was then placed marked side up through the hole of the petri dish top pushing it down until the straws bottom was just shorter than the bottom edges of the top; which suspended the bottom of the straw above the lower portion of the dish. The straw was put in place to be perfectly perpendicular to the lid and then fixed in place using waterproof silicone. The device was allowed to dry for 7 days in a well-ventilated area to allow outgassing of solvent fumes from the silicone, which could potentially damage the embryos. The device was then cleaned with ethanol and rinsed with D.I. water prior to use.

As the microfluidic effect of the chamber was believed to been caused as the embryo dropped through the straw, or tube, variations in exposure to this environment were created by shorting the length of the straw path by cutting the straws to lengths of 99, 66 and 33 mm (¾, ½, and ¼ the length of the original straw, respectively. On days when embryos were weighed, organ culture dishes (Falcon) were fitted with a 5-mm wide flat rubber band, which had been coated with petroleum jelly. The band was used to form an airtight seal between the lid and dish. A complete description of chamber preparation is given below.

Single-cell mouse embryos were then collected from superovulated CB6F1 mice (Charles River; San Diego, Calif.). This strain was selected based on their common use in quality control measures in human IVF laboratories. Following an approved IACUC protocol, the mice were hyperstimulated with a single 0.25-mL subcutaneous injection of 0.5 mIU of PMSG (pregnant mare serum gonadotropin; Sigma Chemical; St. Louis, Mo.) 48 hours prior to embryo retrieval. At 24 hours prior to retrieval, the animals received a second 0.25-mL subcutaneous shot containing 0.5 mIU of hCG (Sigma) to trigger ovulation and the females placed with proven males for mating. Prior to zygote recovery, the mice were euthanized by cervical dislocation and the abdomen was opened sterilely to allow recover of the oviducts. One-cell zygotes were collected from the oviducts into a standard 60-mm petri dish (Falcon) containing a HEPES buffered Hams F-10 media (Irvine; Anaheim, Calif.) with serum substitute supplement for added protein and a penicillin/streptomycin antibiotic mix (Fisher Scientific; Pittsburgh, Pa.) to help prevent possible contamination. After the zygotes were teased out of the oviducts they were transferred to a culture dish containing the same Hams-F10 media mixture. Zygotes were then stored in a non-CO2 incubator at 37° C. until ready to be used.

One day before embryo collections, a standard 60-mm culture dish (Falcon) was prepared by placing five, 30 μL micro droplets of Global media (IVF Online; Guelph, ON N1H 2G6, Canada) with 10% serum substitute supplement (Irvine) under a layer of 7 mL of sterile mineral oil (FertiCult™, Beernem, Belgium). The dish was then placed in a 6% CO2 incubator at 37° C. for a minimum of 18 hours before use for culture of control and dropped embryos. In addition, a bottle of HEPES buffered Hams F-10 with 1.0 mL of serum substitute supplement and 0.1 mL of penicillin/streptomycin antibiotic mix was prepared and placed in a non-CO2 incubator at 37° C. overnight. After embryos were collected, ⅕ of the one-cell embryos were immediately placed into one of the micro-droplets of Global media for culture to serve as a non-manipulated control.

The remaining embryos were held in the Ham's F-10 media until passed through the MSGT. Just prior to use, a series of four MSGT, one of each straw length, were prepared as follows. The lid of each MSGT over the rubber band gasket on the organ culture dish (Falcon). Care was taken to ensure the gasket formed a seal between lid and dish. One milliliter of the Hams F-10 media solution was then loaded into the MSGT through the straw with a 1-mL syringe. Initially, the fluid fell through the straw to the organ culture dish below forming a catchment pool. However, by design, as the pool covered the base of the straw, the pressure created by the seal allowed the media to fill the straw forming a meniscus at the top and creating the drop chamber for the embryos. The prepared device was then placed in front of a specially designed Zeiss Dissection Microscope (Zeiss Instrument; NY, N.Y.) turned 90 degrees from the base to allow viewing of the embryos as they dropped through the marked area on the chamber and allow timing of their descent. The embryos were picked up from the original culture dish containing the Hams F-10 mixture in which they were collected using a 140 µL stripper pipette (Orgio; Charlottesville, Va.). Each embryo for a selected device was picked up and placed one at a time on the meniscus of the Hams F-10 at the top of the chamber. The embryos were then timed as they passed through the 1-cm marked area. Fresh media was added occasionally to attempt to hold constant temperature. Once timing was complete, each embryo was allowed to continue to fall through the chamber to the holding pool formed by media in the organ culture dish. The process was then repeated until all embryos for a single device were dropped through the entire length of the straw.

Once all embryos had been" weighed", the lid to the MSGT was removed and embryos were transferred into their own micro-droplet of GLOBAL MEDIA™. This process was repeated for each of the other three specific gravity devices. To limit any holding effect prior to dropping the embryos through the four different MSGT, the order of the four MSGT units was randomized with each group of animals.

Once all embryos had been transferred to culture media, they were incubated at 6% CO2, 37° C., and 95% relatively for a period of five days, the embryos were then observed at 24-hour intervals for the next four days to determine growth and development. To allow statistical comparisons, embryos were classified as: 1—dead, 2—multicellular (2-16 cells), 3—morula, 4—blastocyst, 5—explained blastocyst, or 6—hatching blastocyst.

A Chi-square analysis compared individual growth rates from each MSGT and control on from each day in culture. Chi-square was chosen as it combines the discrepancies between observed and expected outcomes to determine a P value. The P value to reach significance was established at $P<0.05$. Individual comparisons were made between each treatment and the control within a growth stage with Bonferroni correction.

Additionally, as previous work had determine that the MSGT could suggest the potential growth rate of embryos based upon estimated weight (drop time), a comparison was made of the drop times of individual embryos among the 4 MSGT to ensure any differences between the chambers were not the result of embryo selection, but a true microfluidic type effect.

Previous examples of the present invention have suggested estimated weight (drop time) of embryos may be a beneficial method to select embryos with the highest potential growth rate. Data from the previous study suggested that the embryos with the middleweights range from any individual mouse had the greatest potential for further development. Therefore, to ensure differences seen in growth rates among the four microfluidic (MF) environments (MF-1=33 mm, MF-2=66, mm, MF-3=99 mm, and MF-4=132 mm chambers, respectively) were not due solely to embryo selection, the embryos relative weights were compared among the four devices While results suggest a greater number of embryos exposed to the MF 3 environment were in the heaviest weight range ($P<0.001$) the largest number of embryos in each device (74, 74, 62 and 85% respectively) were in the middleweight range of the cohort. Given the design of the study, it was impossible to compare the weights of the MF chamber embryos to those of the controls.

By day 5 of development the embryos are expected to have reached the hatching blastocyst stage (See FIG. 8). The ability of the blastocyst to be able to hatch out of the zona pellucida is an estimation of its ability to potentially implant within the uterus, due to its need to have the ability to break out of the zona to be able to come in contact with the uterine lining to have any potential for implantation. In these experiments, this stage of development was viewed as the most important in predicting the viability potential of any of the embryos. Data from the present example confirms the initial observation that embryos exposed to the MSGT have improved growth rates over those placed directly into culture after harvest. As the only difference in the culture is the brief period of time the embryo spends dropping through the MSGT, this suggests the environment of the MSGT is responsible for the improve growth rate and that the effect is possibly due to the dynamic nature of the culture; i.e. a microfluidic type effect.

REFERENCES

American Association of Bioanalysts—Embryo Grading Proficiency Testing. http://www.aab-org/pdf/stats/EmbAnds12013/AEF%20Embryo%20Grading%20Qaulitative%201Q2013.pdf Abe H., Yamashita S., Satoh T., Hoshi H. Accumulation of cytoplasmic lipid droplets in bovine embryos and cryotolerance of embryos developed in different culture systems using serum-free or serum-containing media. Mol. Reprod. Dev. 2002; 61: 57-66.

Al Inany H, Aboulghar M, Mansour R, Serour G. Meta-analysis of recombinant versus urinary-derived FSH: an update. Hum Reprod. 2003; 18:305-313. doi: 10.1093/humrep/deg088.

Alfarawati S, Fragouli E, Colls P, Wells D. First births after preimplantation genetic diagnosis of structural chromosome abnormalities using comparative genomic hybridization and microarray analysis. Hum Reprod. 2011; 26:1560-74. doi: 10.1093/humrep/der068.

Alfarawati S, Fragouli E, Colls P, Stevens J, Gutierrez-Mateo C, Schoolcraft W B, Katz-Jaffe M G, Wells D. The relationship between blastocyst morphology, chromosomal abnormality, and embryo gender. Fertil Steril. 2011; 95:520-4.

Baltz J M. Connections between preimplantation embryo physiology and culture. J Assist Reprod Genet. 2013 August; 30(8):1001-7.

Barcelo-Fimbres M., Seidel G. E. Jr. Effects of either glucose or fructose and metabolic regulators on bovine embryo development and lipid accumulation in vitro. Mol. Reprod. Dev. 2007; 74: 1406-1418.

Brezina P R. Preimplantation Genetic Testing in the 21st Century: Uncharted Territory. Clin Med Insights Reprod Health. 2013; 7:17-21.

Brison D R, Houghton F D, Falconer D, Roberts S A, Hawkhead J, Humpherson P G, Lieberman B A, Leese H J. Identification of viable embryos in IVF by non-invasive measurement of amino acid turnover. Hum Reprod 2004; 19:2319-2324.

Bühler K F, Fischer R. Recombinant human LH supplementation versus supplementation with urinary hCG-based LH activity during controlled ovarian stimulation in the long GnRH-agonist protocol: a matched case-control study. Gynecol Endocrinol. 2012 May; 28(5):345-50. doi: 10.3109/09513590.2011.633128.

Centers for Disease Control—Assisted Reproductive Technologies (ART). 2013. http://www.cdc.gov/art/

Chandra A, Martinez G M, Mosher W D, Abma J C, Jones J. Fertility, family planning, and reproductive health of U.S. women: Data from the 2002 National Survey of Family Growth. National Center for Health Statistics. Vital Health Stat 23(25). 2005.

Chavez S L, Loewke K E, Han J, Moussavi F, Colls P, Munne S, Behr B, Reijo Pera R A. Dynamic blastomere behaviour reflects human embryo ploidy by the four-cell stage. Nat Commun. 2012; 3:1251. doi: 10.1038/ncomms2249.

Conaghan J, Chen A A, Willman S P, Ivani K, Chenette P E, Boostanfar R, V L, Adamson G D, Abusief M E, Gvakharia M, Loewke K E, Shen S. Improving embryo selection using a computer-automated time-lapse image analysis test plus day 3 morphology: results from a prospective multicenter trial. Fertil Steril. 2013; 100:412-9.e5. doi: 10.1016/j.fertnstert.2013.04.021.

Das M, Holzer H E. Recurrent implantation failure: gamete and embryo factors. Fertil Steril. 2012 May; 97(5):1021-7. doi: 10.1016/j.fertnstert.2012.02.029.

Deonandan R, Campbell M K, Østbye T, Tummon I. Toward a more meaningful in vitro fertilization success rate. J Assist Reprod Genet. 2000 October; 17(9):498-503.

Ercan C M, Kerimoglu O S, Sakinci M, Korkmaz C, Duru N K, Ergun A. Pregnancy outcomes in a university hospital after legal requirement for single-embryo transfer. Eur J Obstet Gynecol Reprod Biol. 2014; pii: S0301-2115(14)00031-1. doi: 10.1016/j.ejogrb.2014.01.008

Filicori M, Cognigni G. E., Pocognoli P, Tabarelli C, Ferlini F, Perri T, Parmegiani L. Comparison of controlled ovarian stimulation with human menopausal gonadotropin or recombinant follicle-stimulating hormone. Fertil Steril. 2003; 80:390-397. doi: 10.1016/S0015-0282(03)00594-6

Gardner D K, Leese H J. Assessment of embryo viability prior to transfer by the noninvasive measurement of glucose uptake. J Exp Zool 1987; 242:103-105.

Gardner D K, Wale P L. Analysis of metabolism to select viable human embryos for transfer. Fertil Steril. 2013 Mar. 15; 99(4):1062-72. doi: 10.1016/j.fertnstert.2012.12.004.

Geber S, Bossi R, Guimarães F, Valle M, Sampaio M. Effects of transfer of embryos independently cultured in essential and sequential culture media on pregnancy rates in assisted reproduction cycles. J Assist Reprod Genet. 2012 October; 29(10):1097-101. doi: 10.1007/s10815-012-9835-6. Gerris J, De Neubourg D, Mangelschots K, et al. Prevention of twin pregnancy after in-vitro fertilization or intracytoplasmic sperm injection based on strict embryo criteria: a prospective randomized clinical trial. Hum Reprod 1999; 14:2581-2587.

Grace J, El-Toukhy T, Scriven P, Ogilvie C, Pickering S, Lashwood A, Flinter F, Khalaf Y, Braude P. Three hundred and thirty cycles of preimplantation genetic diagnosis for serious genetic disease: clinical considerations affecting outcome. BJOG. 2006; 113:1393-401.

Houghton F D, Hawkhead J A, Humpherson P G, Hogg J E, Balen A H, Rutherford A J, Leese H J. Non-invasive amino acid turnover predicts human embryo developmental capacity. Hum Reprod 2002; 17:999-1005.

Hur Y S, Park J H, Ryu E K, Park S J, Lee J H, Lee S H, Yoon J, Yoon S H, Hur C Y, Lee W D, Lim J H. Effect of micro-vibration culture system on embryo development. J Assist Reprod Genet. 2013; 30:835-41. doi: 10.1007/s10815-013-0007-0.

Kresowik J D, Sparks A E, Van Voorhis B J. Clinical factors associated with live birth after single embryo transfer. Fertil Steril. 2012; 98:1152-6. doi: 10.1016/j.fertnstert.2012.07.1141.

Janvier A, Spelke B, and Barrington K. The Epidemic of Multiple Gestations and Neonatal Intensive Care Unit Use: The Cost of Irresponsibility. J Pediatr 2011; 159: 409-13.

Jones G M, Trounson A, Vella P J, Thouas G A, Lolatgis N, Wood C. Glucose metabolism of human morula and blastocyst-stage embryos and its relationship to viability after transfer. RBM Online 2001; 3:124-132.

Lane M, Gardner D K. Selection of viable mouse blastocysts prior to transfer using a metabolic criterion. Hum Reprod 1996; 11:1975-1978.

Luke B, Brown M B, Wantman E, Lederman A, Gibbons W, Schattman G L, Lobo R A, Leach R E, Stern J E. Cumulative birth rates with linked assisted reproductive technology cycles. N Engl J Med. 2012; 366:2483-91. doi: 10.1056/NEJMoa1110238.

Machtinger R, Racowsky C. Morphological systems of human embryo assessment and clinical evidence. Reprod Biomed Online. 2013; 3:210-21. doi: 10.1016/j.rbmo.2012.10.021.

McArthur S J, Leigh D, Marshall J T, de Boer K A, Jansen R P. Pregnancies and live births after trophectoderm biopsy and preimplantation genetic testing of human blastocysts. Fertil Steril. 2005; 84:1628-36.

Muñoz G, Bongiorni-Malave I. Influence of dietary protein restriction on ovulation, fertilization rates and pre-implantation embryonic development in mice. J Exp Zool. 1979; 210:253-257.

Racowsky C, Vernon M, Mayer J, Ball G D, Behr B, Pomeroy K O, Ball G D, Behr B, Pomeroy K O, Wininger D, Gibbons W, Conaghan J, Stern J E. Standardization of grading embryo morphology. J Assist Reprod Genet. 2010; 27:437-9. doi: 10.1007/s10815-010-9443-2.

Reynolds K A, Omurtag K R, Jimenez P T, Rhee J S, Tuuli M G, Jungheim E S. Cycle cancellation and pregnancy after luteal estradiol priming in women defined as poor responders: a systematic review and meta-analysis. Hum Reprod. 2013; 28:2981-9. doi: 10.1093/humrep/det306.

Sakkas, D. and Gardner, D. K. Noninvasive methods to assess embryo quality. Curr Opin Obstet Gynecol 2005; 17:283-288.

Scott R T Jr, Upham K M, Forman E J, Hong K H, Scott K L, Taylor D, Tao X, Treff N R. Blastocyst biopsy with comprehensive chromosome screening and fresh embryo transfer significantly increases in vitro fertilization implantation and delivery rates: a randomized controlled trial. Fertil Steril. 2013; 100:697-703. doi: 10.1016/j.fertnstert.2013.04.035.

Staessen C, Platteau P, Van Assche E, Miciels A, Tournaye H, Camus M, Devroey P, Liebaers I, van Steirteghem A: Comparison of blastocyst transfer with and without preimplantation genetic diagnosis for aneuploidy screening in couples with advanced maternal age: a prospective randomized controlled trial. Hum Reprod 2004, 19:2849-2858.

Steptoe P C, Edwards R G, Purdy J M. Clinical aspects of pregnancies established with cleaving embryos grown in vitro. Br J Obstet Gynaecol. 1980; 87:757-68.

Smith A L. Blastocyst culture in human IVF: the final destination or a stop along the way? Theriogenology. 2002; 57:97-107.

Smith G D, Monteiro da Rocha A. Advances in embryo culture systems. Semin Reprod Med. 2012; 30:214-21. doi: 10.1055/s-0032-1311523.

Thompson S M, Onwubalili N, Brown K, Jindal S K, McGovern P G. Blastocyst expansion score and trophectoderm morphology strongly predict successful clinical pregnancy and live birth following elective single embryo blastocyst transfer (eSET): a national study. J Assist Reprod Genet. 2013; 12:1577-81. doi: 10.1007/s10815-013-0100-4.

Van den Abbeel E, Balaban B, Ziebe S, Lundin K, Cuesta M J, Klein B M, Helmgaard L, Arce J C. Association between blastocyst morphology and outcome of single-blastocyst transfer. Reprod Biomed Online. 2013; 4:353-61. doi: 10.1016/j.rbmo.2013.07.006.

Weathers, J. (2008) Early Indications of Breed Differences for Cryopreservation of Embryos in Cattle. Master's Thesis. repositories.tdl.orghtu-ir/bitstream/handle/2346/18883/Weathers_Julie_Thesis.pdf?sequence=1

Weathers, N. Zimmerer N., Penrose L., Graves-Evenson K., Prien, S. The relationship between maternal body fat and pre-implantation embryonic weight: Implications for survival and long-term development in an assisted reproductive environment. Open J Ob Gyn, 2013, 3; 1-5. doi: 10.4236/ojog.2013.35A2001.

What is claimed is:

1. A method of non-invasive selection and recovery of viable mammalian embryos having enhanced embryo development, comprising:

descending a plurality of embryos through a drop chamber comprising a lumen containing a biocompatible media composition extending vertically from a recovery pool having fluid communication with the lumen of the drop chamber, wherein the recovery pool is capable of receiving the embryos from the lumen of the drop chamber, allowing for embryo recovery;

measuring the plurality of embryos while descending through a predetermined timing zone of said drop chamber having an upper and lower boundary of said predetermined timing zone, wherein said measuring step comprises:
 a. detecting the movement downward of each embryo through the biocompatible media composition in the drop chamber, and
 b. identifying descent time of each embryo moving downward through the biocompatible media composition between the upper and lower boundaries of said predetermined timing zone to determine the estimated weight of each embryo, wherein a faster descent time indicates a higher estimated weight, selecting at least one of the plurality of embryos having a higher estimated weight; and recovering said at least one embryo selected from the recovery pool, wherein the at least one embryo recovered has enhanced viability and embryo development.

2. The method of claim 1, wherein said measuring step further comprises:
 c. determining specific gravity of the plurality of embryos by measuring the descent time of each embryo through the biocompatible media composition within the upper and lower boundary of said predetermined timing zone of the drop chamber capable of detection by a means selected from the group consisting of: visual means, tagging of the embryos, markers detected on or in the embryos, computerized means of embryo recognition utilizing a processor having programmable logic designed to detect each embryo during descent through the timing zone, or combinations thereof.

3. The method of claim 1, further comprising comparing the identified descent time of each embryo in measuring step b to the mean or median descent times of a plurality of embryos of the same species which were previously measured, wherein a faster descent time further indicates a higher specific gravity and the at least one embryo selected further has a higher specific gravity than the mean or median of the plurality of embryos.

4. The method of claim 1, wherein the plurality of embryos range from zygote to blastocyst stage.

5. The method of claim 4, further comprising comparing the identified descent time of each embryo ranging from zygote to blastocyst stage in measuring step b within a population mean wherein a faster descent time indicates a higher estimated weight.

6. The method of claim 1, further comprising utilizing one or more drop chambers, for assessing one or more embryos, each of the one or more drop chambers emptying into one or more recovery pools to allow selection and recovery of one or more embryos having separate identifications.

7. The method of claim 1, wherein said plurality of embryos comprises cryopreserved embryos, and the at least one embryo selected will survive after thaw.

8. The method of claim 1, wherein said measuring step performed by descending the embryos through the biocompatible media composition of the drop chamber does not reduce the viability of the plurality of embryos.

* * * * *